(12) United States Patent
Karl et al.

(10) Patent No.: US 7,420,088 B2
(45) Date of Patent: Sep. 2, 2008

(54) METHOD FOR THE PRODUCTION OF FORMIC ACID

(75) Inventors: Jorn Karl, Ludwigshafen (DE); Alexander Hauk, Ludwigshafen (DE)

(73) Assignee: BASF Aktiengesellschaft (DE)

(*) Notice: Subject to any disclaimer, the term of this patent is extended or adjusted under 35 U.S.C. 154(b) by 62 days.

(21) Appl. No.: 11/574,069

(22) PCT Filed: Aug. 22, 2005

(86) PCT No.: PCT/EP2005/009066

§ 371 (c)(1),
(2), (4) Date: Feb. 22, 2007

(87) PCT Pub. No.: WO2006/021411

PCT Pub. Date: Mar. 2, 2006

(65) Prior Publication Data

US 2008/0097126 A1    Apr. 24, 2008

(30) Foreign Application Priority Data

Aug. 23, 2004    (DE) ................. 10 2004 040 789

(51) Int. Cl.
*C07C 53/00* (2006.01)
(52) U.S. Cl. .................................... 562/609
(58) Field of Classification Search ............. None
See application file for complete search history.

(56) References Cited

U.S. PATENT DOCUMENTS

| 1,919,850 A | 7/1933 | Lüscher |
| 2,511,198 A | 6/1950 | Engel |
| 3,414,610 A | 12/1968 | Wagner et al. |
| 4,218,568 A | 8/1980 | Hohenschutz et al. |
| 5,294,740 A | 3/1994 | Kiefer et al. |

FOREIGN PATENT DOCUMENTS

| DE | 3428-319 | 2/1986 |
| EP | 0 001 432 | 4/1979 |
| EP | 0 095 321 | 11/1983 |
| EP | 0 151 510 | 8/1985 |
| EP | 0 357 243 | 3/1990 |
| EP | 0 563 831 | 10/1993 |
| GB | 1028930 | 5/1966 |

OTHER PUBLICATIONS

International Search Report No. PCT/EP2005/009066.

*Primary Examiner*—Karl J Puttlitz
(74) *Attorney, Agent, or Firm*—Connolly Bove Lodge & Hutz LLP

(57) ABSTRACT

The present invention relates to a process for preparing formic acid by thermally decomposing ammonium formates of tertiary amines A, wherein the tertiary amine A on which the ammonium formate is based has a boiling point at atmospheric pressure in the range from 105 to 175° C.

12 Claims, 1 Drawing Sheet

METHOD FOR THE PRODUCTION OF FORMIC ACID

CROSS REFERENCE TO RELATED APPLICATION

Figure 1:
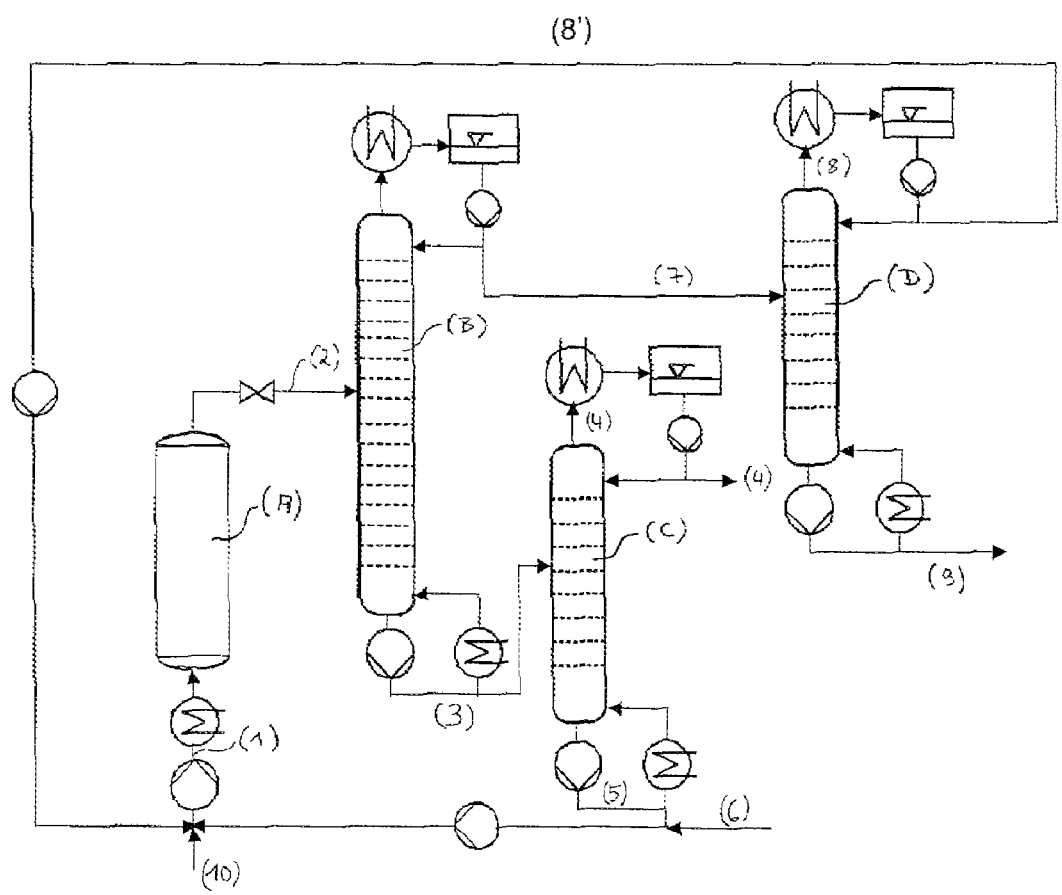

The present application is a National Stage application of PCT/EP2005/009066, which claims priority from German Patent Application No. DE 102004040789.4, filed Aug. 23, 2004.

The present invention relates to a process for preparing formic acid by thermally decomposing ammonium formates of tertiary amines.

The preparation of formic acid by thermally decomposing ammonium formates of tertiary amines A according to the following reaction equation

is known in principle. For example, EP-A 1432 describes a process in which an ammonium formate of a tertiary amine is initially prepared by hydrolyzing methyl formate in the presence of a tertiary amine which boils at at least 180° C. at atmospheric pressure in an amount of from 0.5 to 3.0 mol per mole of methyl formate. Tertiary amines suitable for this purpose which are proposed are imidazole compounds. However, in-house investigations have shown that these imidazole compounds are not sufficiently stable under process conditions. In addition, the thus prepared formic acid becomes discolored when left to stand.

To solve the problems which occur in the process of EP-A 1432, EP-A 563831 proposes carrying out the thermal dissociation in the presence of secondary formamides which should have a boiling point from 30 to 150 K lower than the tertiary amine present in the ammonium formate. These tertiary amines are high-boiling substances having a boiling point at atmospheric pressure of above 200° C. Moreover, the formic acid obtained by this process likewise tends to discoloration.

It is therefore an object of the present invention to provide a process for preparing formic acid, in which formic acid is obtained which only has a very much lower, if any, tendency to discolor than in the prior art. The process should additionally be economically viable, i.e. it should be possible to carry it out especially with high yields based on the starting materials, good space-time yields and low energy demands.

It has been found that, surprisingly, these objects can be achieved by thermally cleaving ammonium formates of tertiary amines A which have a boiling point at atmospheric pressure in the range from 105 to 175° C.

Accordingly, the present invention relates to a process for preparing formic acid by thermally dissociating ammonium formates of tertiary amines A, wherein the tertiary amine A on which the ammonium formate is based has a boiling point at atmospheric pressure in the range from 105 to 175° C.

The term "tertiary amine" includes here and hereinbelow both tertiary amines which have at least one tertiary nitrogen atom which has three aliphatic or cycloaliphatic substituents which may form a mono- or bicyclic ring skeleton with the nitrogen atom and nitrogen compounds in which the tertiary nitrogen atom is incorporated into an aromatic ring skeleton.

Among these amines, preference is given to those whose $pK_a$ in water at standard pressure and standard temperature is in the range from 4 to 9. With regard to the definition of the $pK_a$, reference is made at this point to Landoldt-Börnstein, 6th edition, volume II, p. 900 ff. The amines A have typically 1 or 2 tertiary nitrogen atoms, in particular 1 nitrogen atom, and from 6 to 10 carbon atoms and also, if appropriate, 1 or 2 oxygen atoms.

Among the tertiary amines are pyridine compounds, especially mono-, di- and tri-$C_1$-$C_4$-alkylpyridines having preferably a total of 6 to 10 carbon atoms, such as α-picoline, β-picoline, γ-picoline, 2,4,6-trimethylpyridine, 2,3,5-trimethylpyridine, 2-, 3- and 4-tert-butylpyridine, 2,6-dimethylpyridine, 2,4-dimethylpyridine, and also phenyl-, pyridyl-, benzyl-, pyridylmethyl- or pyridylethyl-substituted pyridine such as 2,2'-bipyridine, 4,4'-bipyridine, 2-, 3- or 4-phenylpyridine, 2-, 3- or 4-benzylpyridine, bis(4-pyridyl)methane and 1,2-bis(4-pyridyl)ethane, and also 4-dialkylaminopyridines such as 4-dimethylaminopyridine and 4-diethylaminopyridine, and also mono- and di-$C_1$-$C_4$-alkoxypyridines such as 2,6-dimethoxypyridine are preferred.

Preference is further given to what are known as bridged amines, i.e. tertiary amines in which the amine nitrogen atom is a ring member of a saturated 5- to 8-membered cycle and in particular the bridgehead atom of a bicyclic ring system having preferably from 6 to 10 carbon atoms. Examples thereof are 1-azabicyclo[2.2.2]octane, 9-benzyl-9-azabicyclo[3.3.1]nonane, 3-methyl-3-azabicyclo[3.3.0]octane and 8-methyl-8-aza-bicyclo[3.2.1]octane. Also suitable are saturated, 5-, 6-, 7- or 8-membered nitrogen heterocycles which bear an N-$C_1$-$C_4$-alkyl group on the at least one nitrogen atom and which may also have an oxygen atom as a ring member, such as N-methylpyrrolidine, N-ethylpyrrolidine, N-propylpyrrolidine, 1-(2-propylpyrrolidine), N-methylpiperidine, N-ethylpiperidine, N-propylpiperidine, N-methylmorpholine, N-ethylmorpholine, 1-butylpyrrolidine and the like.

However, also suitable in principle are amines of the following general formula I

where
  $R^1$, $R^2$ and $R^3$ are each independently $C_1$-$C_6$-alkyl such as methyl, ethyl, propyl, isopropyl, n-butyl, 2-butyl, isobutyl, tert-butyl, n-pentyl and n-hexyl, $C_5$-$C_8$-cycloalkyl such as cyclopentyl, cyclohexyl, cycloheptyl and cyclooctyl, aryl which optionally bears one or two $C_1$-$C_4$-alkyl groups as substituents, for example phenyl, or tolyl, or phenyl-$C_1$-$C_4$-alkyl such as benzyl or phenethyl.

In the compounds of the formula I, the total number of carbon atoms is generally from 7 to 10. Examples of compounds I are N,N-dimethylcyclohexylamine, tripropylamine, N-ethyl-N-propylaminepropane, N,N-dimethylaniline and N,N-diethylaniline.

The quaternary ammonium formate used for the thermal dissociation may be prepared by processes known per se:
  i) by directly reacting the corresponding tertiary amine A with formic acid in analogy to the processes described in GB-A 1028930 or U.S. Pat. No. 3,414,610,
  ii) by transition metal-catalyzed hydrogenation of carbon dioxide to formic acid in the presence of the tertiary amine A in analogy to the processes described in EP-A 95321, EP-A 151510 or EP-A 357243,
  iii) by reacting methyl formate with water and subsequently extracting the formic acid formed with the tertiary amine A in analogy to the method in DE-A 3428319 or iv) by reacting methyl formate with water in the presence of the tertiary amine in analogy to the method of EP-A 1432.

The crude products obtained by processes i) to iv) comprise, in addition to the particular ammonium formate, depending upon the process selected in each case, further compounds, for example organic solvents, unconverted starting materials, for example methyl formate, coproducts formed, for example methanol, and/or catalyst components. For example, the reaction mixtures obtained by the process iv) comprise, in addition to the ammonium formate of the tertiary amine A used for the hydrolysis, as further compounds, generally also water, methanol and/or methylformate.

It is recommended to remove these constituents before the inventive thermal decomposition of the ammonium formate substantially, preferably fully or virtually fully, in particular to an extent of at least 99% and more preferably to an extent of at least 99.9% and especially to an extent of at least 99.95%, based on the total amount of the resulting impurities, or to reduce them to a residual content of less than 1% by weight, in particular less than 0.1% by weight and especially to from 100 to 500 ppm, based on the ammonium formate fed to the thermal dissociation. Data in ppm here and hereinbelow are $10^{-6}$ parts by weight.

For the thermal dissociation of the ammonium formates, an ammonium formate-containing crude product, if appropriate after substantial removal of unconverted reactants and coproducts or other volatile impurities, for example unconverted methyl formate, methanol and, where present, water, will generally be heated to a temperature at which dissociation of the ammonium formate into formic acid and tertiary amine A takes place. The thermal dissociation will preferably be conducted in such a way that the temperature of the mixture does not exceed 130° C. and in particular 125° C., and is in particular in the range from 90 to 125° C. The thus released formic acid is removed from the reaction mixture in a customary manner. Appropriately, the formic acid is removed by distilling off the formic acid, if appropriate together with water, from the reaction mixture used. In order to ensure distillation of the formic acid out of the reaction mixture, the ammonium formate is preferably thermally dissociated at a pressure of not more than 1.1 bar, for example in the range from 0.01 to 1 bar, in particular in the range from 0.02 to 0.8 bar and more preferably in the range from 0.05 to 0.5 bar.

Suitable apparatus for the thermal dissociation of the ammonium formate is in principle distillation apparatus in particular, such as distillation columns, for example columns having random packing and bubble-cap tray columns. Suitable random packings are in particular structured packings, glass rings, Raschig rings and Pall rings, and preference is given to ceramic random packings to avoid corrosion.

In one embodiment of the process according to the invention, the thermal dissociation is carried out in the presence of a formamide of a secondary amine. Suitable formamides are in particular the compounds of the general formula II specified in EP-A-563831, especially those whose boiling points do not exceed 170° C. at atmospheric pressure. Examples of such formamides are in particular N-formylmorpholine, N-formylpyrrolidine, N-formylpiperidine, N,N-dimethylformamide and N,N-diethyl-formamide. In another preferred embodiment, the thermal dissociation is carried out in the absence of the formamide.

Advantageously, the process according to the invention is configured as a continuous process. To this end, the reactor effluent of the ammonium formate synthesis which generally still contains volatile constituents is fed appropriately to a first distillation apparatus, in which the majority of volatile constituents is distilled off overhead preferably to a residual content of not more than 1% by weight, in particular not more than 0.1% by Weight and especially not more than 500 ppm. The bottom draw of the first distillation apparatus is then fed to a second distillation apparatus for the thermal dissociation of the ammonium formate. In this second distillation apparatus, the pressure conditions are those specified above for the ammonium formate dissociation. The temperature of the column bottom has the temperatures specified above for the thermal dissociation of the ammonium formate and is in particular in the range from 90 to 120° C. In this second distillation apparatus which is appropriately configured as a column having preferably from 15 to 30 and in particular having from 20 to 25 theoretical plates, formic acid and, where present, water are then distilled off overhead. The column bottoms comprise substantially the tertiary amine A used, with or without traces of formic acid. The bottoms are therefore recycled appropriately into the preparation process of the ammonium formate.

In a preferred embodiment of the process according to the invention, the thermal dissociation is effected using an ammonium formate which has been prepared by hydrolyzing methyl formate in the presence of the tertiary amine A. Accordingly, a preferred embodiment of the process according to the invention comprises the hydrolysis of methyl formate in the presence of the tertiary amine A and the thermal dissociation of the thus obtained ammonium formate of the tertiary amine A.

The hydrolysis is effected generally by reacting methyl formate with water, in the presence of from 0.5 to 3 mol, preferably from 0.8 to 1.5 mol and in particular from 0.9 to 1.2 mol of tertiary amine A, based on 1 mol of methyl formate. When the amine A is used in deficiency based on the methyl formate, the reaction mixture is a mixture of formic acid and ammonium formate which can be used for the thermal dissociation, especially when the intention is not to prepare anhydrous formic acid.

The amount of water required to achieve sufficient conversions is generally at least 0.8 mol per mole of methyl formate and is typically in the range from 0.8 to 1.2 mol of water per mole of methyl formate.

In general, the hydrolysis is effected at temperatures in the range from 50 to 200° C., preferably in the range from 70 to 160° C. Owing to the volatility of the methyl formate—the boiling point is 32° C. at atmospheric pressure—the hydrolysis is effected generally under elevated pressure, typically at a pressure in the range from 1.1 to 50 bar, in particular in the range from 2 to 30 bar and especially in the range from 3 to 20 bar. Typically, the hydrolysis is conducted up to a conversion of at least 50%, based on methyl formate used, and in particular up to a conversion of from 60 to 95%. Accordingly, the reaction product comprises, in addition to the ammonium formate and methanol formed in the reaction, methyl formate which is yet to be converted, with or without water.

It is recommended to remove unconverted methyl formate and methanol from the reaction mixture before the thermal dissociation of the ammonium formate. This is effected typically by distillative workup of the reaction mixture, in which at least the majority of the methanol formed in the reaction and of any methyl formate present in the reaction mixture are distilled out of the reaction mixture, preferably down to a residual content of these constituents of not more than 0.1% by weight and in particular not more than 0.5 ppm, and the resulting distillation residue which consists substantially of ammonium formate, with or without formic acid and water, is fed subsequently to the thermal dissociation.

To carry out the hydrolysis, the procedure may be, for example, to initially react methyl formate and water and a portion, for example from 20 to 80%, of the amine with one another under the reaction conditions and subsequently to add the remainder of amine until the desired conversion has been attained. However, preference is given to reacting methyl formate, water and amine with one another in the desired ratio.

Advantageously, hydrolysis and subsequent thermal dissociation are configured as continuous process. To this end, the methyl formate is initially fed together with the desired amount of water and tertiary amine A to a first reaction zone under the reaction conditions specified above. The residence time in the first reaction zone is selected such that the abovementioned conversions are attained. The reactor effluent of the hydrolysis reaction which, in addition to methanol, generally also comprises methyl formate and water as further constituents is appropriately fed to a first distillation apparatus, in which the majority of methyl formate and methanol are distilled off overhead, preferably down to a residual content of not more than 0.1% by weight and in particular not more than 500 ppm, for example down to a residual content of from 100 to 500 ppm. The first distillation apparatus is generally configured as a column having from 20 to 30 theoretical plates. Those skilled in the art will select the pressure such that the bottom temperature of the first distillation apparatus preferably does not exceed 130° C. and in particular 125° C. Typically, the pressure is not more than 1.1 bar. The bottom draw of the first distillation column is then, as described above, fed to a second distillation apparatus for the thermal dissociation of the ammonium formate, in the course of which formic acid and, where present, water are distilled off overhead. The bottoms may then be fed back to the hydrolysis reaction. With regard to the pressure and temperature conditions in the second column, the above statements on the thermal dissociation apply correspondingly.

The distillate of the first column, when it still comprises methyl formate, may be subjected to a further distillation to separate methanol and methyl formate. The methyl formate which is obtained may likewise by recycled into the hydrolysis reaction.

The process according to the invention allows an efficient preparation of formic acid which, in contrast to the formic acid obtained in accordance with the prior art, only has a very slight, if any, tendency to discolor even in the course of prolonged standing. In addition, the process is more economic in comparison to the existing processes, since the temperatures required for the thermal dissociation are lower than in the prior art. The process affords formic acid in high yield, based on the starting materials, and can be carried out efficiently with high space-time yields. Since it is possible to recycle the base used, the costs for the process can be reduced further.

FIG. 1 which follows and the example illustrate the process according to the invention in more detail.

FIG. 1 shows a schematic of a continuous configuration of the process according to the invention, in which ammonium formate is prepared by hydrolyzing methyl formate with water in the presence of the tertiary amine. To this end, water, methyl formate and tertiary amine are fed into the hydrolysis reactor A as stream 1. The reactor effluent is decompressed and fed into the distillation column B. The distillation residue of column B which comprises ammonium formate and water is fed into a further distillation column C as stream 3. In column C, the thermal dissociation of the ammonium formate takes place, and aqueous formic acid is drawn off at the top of the column in a concentration of from 70 to 85% by weight (stream 4). The distillation residue of column C which comprises substantially the tertiary amine A and small amounts of formic acid is drawn off as stream 5, if appropriate enriched with fresh base (stream 6) and combined with the water and methyl formate starting materials (stream 10) and recycled into the hydrolysis reaction as stream 1.

At the top of the column B, the methanol present in the reactor effluent (2) of the hydrolysis A and any unconverted methyl formate are drawn off and fed to a distillative separation into methyl formate and methanol (column D) as stream (7). The unconverted methyl formate is drawn off at the top of column D as stream (8) and combined via (8') with the stream of the starting materials (stream 1) and recycled thus into the hydrolysis A. Substantially pure methanol is obtained as the bottoms of column D and is discharged as stream 9 and can be fed to other uses, for example the preparation of methyl formate.

EXAMPLE

General Method for the Hydrolysis of Methyl Formate and Subsequent Thermal Decomposition of the Resulting Ammonium Formate In a continuous stirred vessel having a reactor capacity of 200 ml, a mixture of methyl formate, water and 2,6-dimethylpyridine in a molar ratio of 1:1:0.9 was fed at a feed rate of 570 g/h. The reactor temperature was 120° C. and the pressure 12 bar.

The reaction mixture was decompressed into the middle of a bubble-cap tray column having a diameter of 30 mm and a height of 3 m (30 bubble-caps), so that a mixture of 78 g/h of methanol and 56 g/h of methyl formate was drawn off at a top temperature of 43° C. and a reflux ratio of 2.

The bottom product of the first column was introduced into a randomly packed column (diameter 30 mm, height 2 m, reflux ratio 3) operated at 400 mbar. The bottom temperature was about 125° C. At a top temperature of 79.5° C., 120 g/h of a mixture of formic acid and water distilled off at a formic acid content of 85%. The bottom product obtained was the tertiary amine which contained up to about 3% by weight formic acid. This was recycled quantitatively into the hydrolysis reaction.

The resulting formic acid had a low color number which did not rise even after several days of storage.

What is claimed is:

1. A process for preparing formic acid by thermally decomposing ammonium formates of tertiary amines A, wherein the tertiary amine A is a pyridine compound which has a boiling point at atmospheric pressure in the range from 105 to 175° C. and wherein the ammonium formate is prepared by hydrolyzing methyl formate in the presence of the tertiary amine A.

2. The process according to claim 1, wherein the tertiary amine A has a $pK_a$ in water at 25° C. in the range from 4 to 9.

3. The process according to claim 1, wherein the decomposition of the ammonium formate is carried out at a reaction temperature of not more than 130° C.

4. The process according to claim 1, wherein the thermal decomposition is configured as a distillation in which formic acid and, where present, water are distilled out of the ammonium formate-containing reactant.

5. The process according to claim 1, wherein the hydrolysis of the methyl formate is carried out up to a conversion in the range from 50 to 95%.

6. The process according to claim 1, wherein the mixture obtained in the hydrolysis is subjected to a first distillation in which the majority of methanol and any unconverted methyl formate are distilled out of the mixture obtained in the hydrolysis, and the resulting residue is subjected to a second distillation to decompose the ammonium formate, in which formic acid and, where present, water are distilled off.

7. The process according to claim 1, wherein the tertiary amine A is recycled into the reaction.

8. The process according to claim 2, wherein the decomposition of the ammonium formate is carried out at a reaction temperature of not more than 130° C.

9. The process according to claim 1, wherein the decomposition of the ammonium formate is carried out at a reaction temperature of not more than 130° C.

10. The process according to claim 2, wherein the thermal decomposition is configured as a distillation in which formic acid and, where present, water are distilled out of the ammonium formate-containing reactant.

11. The process according to claim 1, wherein the thermal decomposition is configured as a distillation in which formic acid and, where present, water are distilled out of the ammonium formate-containing reactant.

12. The process according to claim 3, wherein the thermal decomposition is configured as a distillation in which formic acid and, where present, water are distilled out of the ammonium formate-containing reactant.

* * * * *